United States Patent
Uckun et al.

(10) Patent No.: US 6,642,221 B1
(45) Date of Patent: Nov. 4, 2003

(54) VANADIUM COMPOUNDS AS ANTI-PROLIFERATIVE AGENTS

(75) Inventors: Faith M Uckun, White Bear Lake, MN (US); Christopher S Navara, Plymouth, MN (US)

(73) Assignee: Parker Hughes Institute, Roseville, MN (US)

( * ) Notice: Subject to any disclaimer, the term of this patent is extended or adjusted under 35 U.S.C. 154(b) by 111 days.

(21) Appl. No.: 09/713,544

(22) Filed: Nov. 15, 2000

(51) Int. Cl.$^7$ .................. A61K 31/555; A61K 31/28; A61K 33/24
(52) U.S. Cl. .............. 514/185; 514/184; 514/188; 514/492; 514/863; 514/883; 514/908; 424/646
(58) Field of Search .................. 514/492, 863, 514/184, 185, 188, 883, 908; 424/646

(56) References Cited

U.S. PATENT DOCUMENTS

| | | | |
|---|---|---|---|
| 4,559,157 A | 12/1985 | Smith et al. | 424/401 |
| 4,608,392 A | 8/1986 | Jacquet et al. | 514/772 |
| 4,820,508 A | 4/1989 | Wortzman | 424/59 |
| 4,938,949 A | 7/1990 | Borch et al. | 514/476 |
| 4,992,478 A | 2/1991 | Geria | 514/782 |
| 4,994,445 A | * 2/1991 | Le Ribault et al. | 514/63 |
| 5,871,779 A | * 2/1999 | Cruz | 424/646 |

FOREIGN PATENT DOCUMENTS

| | | |
|---|---|---|
| WO | WO 99/36063 | 7/1999 |
| WO | WO 00/27389 | 5/2000 |
| WO | WO 00/25930 | 6/2000 |

OTHER PUBLICATIONS

Chemical Abstracts 96:79536 (1982).*

Westerfield, M., "The Zebrafish Book. A Guide for the Laboratory Use of Zebrafish (*Danio rerio*)", Edition 4 (2000).

Balczon, R. et al., "Dissocation of Centrosome Replication Events from Cycles of DNA Synthesis and Mitotic Division in Hydroxyurea–arrested Chinese Hamster Ovary Cells", *The Journal of Cell Biology*, vol. 130, No. 1, pp. 105–115 (Jul., 1995).

Balczon, R., "The Centrosome in Animal Cells and Its Functional Homologs in Plant and Yeast Cells", *International Review of Cytology*, vol. 169, pp. 25–82 (1996).

Benyumov, A. et al., "Duration of the First Mitotic Cycles and Staging of Embryogenesis in *Danio rerio*", *Russian Journal of Development Biology*, vol. 26, No. 2, pp. 106–111 (1995).

Byers, B., "Mutiple Roles of the Spindle Pole Bodies in the Life Cycle of *Saccharomyces cerevisiae*", *Molecular Genetics in Yeast*, pp. 119–133 (1981).

Cahill, D. et al., "Mutations of Mitotic Checkpoint Genes in Human Cancers", *Nature*, vol. 392, pp. 300–303 (Mar. 19 1998).

Church, K. et al., "Micromanipulated Bivalents Can Trigger Mini–Spindle Formation in *Drosophila melangaster* Spermatocyle Cytoplasm", *The Journal of Cell Biology*, vol. 103, No. 6, Pt. 2, pp. 2765–2773 (Dec., 1986).

Doyle, G. et al., "Pseudohalide and Chelate Complexes of Bis(cyclopentadienyl)vanadium(IV)", *Inorganic Chemistry*, vol. 7, No. 12, pp. 2479–2484 (Dec., 1968).

Glover, D. et al., "Mutations in *aurora* Prevent Centrosome Separation Leading to the Formation of Monopolar Spindles", *Cell*, vol. 81, pp. 95–105 (Apr. 7, 1995).

Gorbsky, G., "Cell Cycle Checkpoints: Arresting Progress in Mitosis", *BioEssays*, vol. 19, No. 3, pp. 193–197 (Mar., 1997).

Hardwick, K., "The Spindle Checkpoint", *TIG*, vol. 14, No. 1, pp. 1–4 (Jan., 1998).

Hoyt, M. et al., "*S. cerevisiae* Genes Required for Cell Cycle Arrest in Response to Loss of Microtubule Function", *Cell*, vol. 66, No. 3, pp. 507–517 (Aug. 9, 1991).

Khan, S. et al., "p53 and pRb Prevent Rereplication in Response to Microtubule Inhibitors by Mediating a Reversible $G_1$ Arrest", *Cancer Research*, vol. 58, No. 3, pp. 396–401 (Feb. 1, 1998).

Kopf–Maier, P. et al., "Induction of Cell Arrest at $G_1$/S and in $G_2$ After Treatment of Ehrlich Ascites Cells with Metallocene Dichlorides and cis–Platinum in vitro", *Journal of Cancer Research and Clinical Oncology*, vol. 106, No. 1, pp. 44–52 (1983).

Lanni, J. et al., "Characterization of the p53–Dependent Postmitotic Checkpoint following Spindle Disruption", *Molecular and Cellular Biology*, vol. 18, No. 2, pp. 1055–1064 (Feb., 1998).

Li, R. et al., "Feedback Control of Mitosis in Budding Yeast", *Cell*, vol. 66, No. 3, pp. 519–531 (Aug. 9 1991).

Sakurai, H. et al., "Mechanism for a New Antitumor Vanadium Complex: Hydroxyl Radical–Dependent DNA Cleavage by 1,10–Phenanthroline–Vanadyl Complex in the Presence of Hydrogen Peroxide", *Biochemical and Biophysical Research Communications*, vol. 206, No. 1, pp. 133–137 (Jan. 5, 1995).

Schatten, G., "The Centrosome and Its Mode of Inheritance: The Reduction of the Centrosome during Gametogenesis and Its Restoration during Fertilization", *Developmental Biology*, vol. 165, No. 2, pp. 299–335 (Oct. 1994).

Sullivan, W. et al., "*daughterless–abo–like*, a Drosphila Maternal–Effect Mutation that Exhibits Abnormal Centrosome Separation during the Late Blastoderm Divisions", *Development* vol. 110, No. 2, pp. 311–323 (Oct., 1990).

(List continued on next page.)

Primary Examiner—John Pak
(74) Attorney, Agent, or Firm—Merchant & Gould P.C.

(57) ABSTRACT

Vanadium compounds as anti-proliferative agents. These compounds act to disrupt mitotic and meiotic spindle formation and thus are useful to prevent cell mitosis (proliferation) and meiosis.

7 Claims, No Drawings

OTHER PUBLICATIONS

Vaisberg, E. et al., "Cytoplasmic Dynein Plays a Role in Mammalian Mitotic Spindle Formation", *The Journal of Cell Biology*, vol. 123, No. 4, pp. 849–858 (Nov., 1993).

Westerfield, M., "The Zebrafish Book: A Guide to the Laboratory Use of Zebrafish Danio Brachrerio", 3rd ed., University of Oregon Press, Eugene, 26 pages (1995).

Wilkinson, G. et al., "Bis–cyclopentadienyl–Compounds of Ti, Zr, V, Nb and Ta", *The Journal of the American Chemical Society*, vol. 76, pp. 4281–4284 (Sep. 5, 1954).

Winey, M. et al., "MPS1 ands MPS2: Novel Yeast Genes Defining Distinct Steps of Spindle Pole Body Duplication", *The Journal of Cell Biology*, vol. 114, No. 4, pp. 745–754 (Aug., 1991).

* cited by examiner

VANADIUM COMPOUNDS AS ANTI-PROLIFERATIVE AGENTS

BACKGROUND OF THE INVENTION

All proliferating eucaryotic cells must undergo a process termed mitosis before separating into two new cells. Mitosis is a process in which the parent or replicating cell undergoes a series of molecular events that results in the formation of two nuclei in the place of one. Traditionally, mitosis has been described as a series of six dynamic stages: prophase, prometaphase, metaphase, anaphase, telophase and cytokinesis. Briefly, mitosis begins in prophase with the formation of the mitotic spindle having two centrosomes and associated microtubules. During prometaphase and metaphase the centrosomes migrate to opposite ends of the cell to form two spindle poles, followed by the previously duplicated chromosomes aligning at the metaphase plate in-between the two poles. One of each duplicated chromosomes is separated to each pole, nuclei are re-form containing the complement of chromosomes, and the cytoplasm cleaved in half to form two separate daughter cells.

Critical to the separation of the replicated chromosomes and formation of the two nuclei in the mitotic process is the bipolar mitotic spindle. Cells must properly form a bipolar mitotic spindle with bivalent chromosomes properly attached to each pole of the spindle (Gorbsky et al, *Bioessays*, 19: 193–197, 1997; Hardwick, K. G., *Trends Genet.*, 14: 1–4, 1998). Cells which do not form a correct mitotic spindle arrest at metaphase of mitosis indefinitely or progress into apoptosis. Several proteins from yeast and mammals have been implicated in this process; MAD1 (mitotic arrest deficient), MAD2, and MAD3 (Li et al, *Cell*, 66: 519–531, 1991 (published erratum appears in *Cell*, 79(2), following p388)), BUB1 (budding uninhibited by benzimidazole), BUB2 and BUB3 (Hoyt et al, *Cell*, 66: 507–517, 1991). Mammalian counterparts for these proteins include HsMAD2 (Li et al, Supra) and hBUB1 (Cahill et al, *Nature*, 392: 300–303, 1998).

One of the most crucial and tightly regulated events during mitosis is centrosome duplication (Schatten, G., *Dev. Biol.*, 165: 299–335, 1994; Balczon, R., *International Review of Cytology*, 169: 25–82, 1996). The centrosome is an organelle consisting of a pair of centrioles surrounded by an amorphous electron dense material and represents the mammalian equivalent of the yeast spindle pole body. This organelle serves as a site of microtubule organization in the cell. During cell cycle progression the centrosome duplicates, separates and functions as the poles for the mitotic spindle. It is crucial for proper chromosome segregation and fidelity that centrosome replication be tightly regulated, doubling just once during each cell cycle. Centrosome regulation is tightly linked to the S-phase checkpoint (Khan et al., *Cancer Res.*, 58: 396–401, 1998; Lanni et al., *Mol. Cell Biol.*, 18: 1055–1064, 1998). For example blocking cells at the beginning of S-phase leads to the formation of multiple centrosomes (Baczon et al., *J. Cell Biol.*, 130: 105–115, 1995).

Considerable efforts are underway to develop new anti-proliferative agents for use as therapies in the treatment of cancer, as well as non-cancer proliferative disorders such as epithelial hyperplasia, polycytemia, erythrocytemia, thrombocytemia, EBV transformed lymphoproliferative syndrome, dysplastic nevus syndrome, restenosis after angioplasty for coronary heart disease, mastocytosis, histiocytosis, psoriasis, polyps, and the like. One target for anti-proliferative agents is the mitotic pathway. Accordingly, there is a need for the development of novel, effective anti-proliferative agents that target the mitotic pathway.

Vanadocene dichloride (VDC) has been shown to arrest tumor cell growth (Kopf-Maier, et al, *J. Cancer Res. Clin. Onccol.*, 106: 44–52. 1983), and the oxovanadium compound, [VO(Phen)($H_2O$)$_2$]($SO_4$), has been shown to be an active agent against pharyngonasal cancer as determined by a single assay (Sakurai, et. al, *BBRC*, 206; 133, 1995). Vanadium compounds have also been shown to induce apoptosis in certain cancer cells (Uckun et al., WO 00/35930).

Against this backdrop the present invention has been developed.

SUMMARY OF THE INVENTION

It has now been found that vanadium compounds of the invention, and particularly vanadium compounds and oxovanadium compounds described herein, are effective anti-proliferation agents. These compounds act to disrupt mitotic and meiotic spindle formation and thus are useful to prevent cell mitosis (proliferation) and meiosis.

The invention provides a method for disrupting mitosis or meiosis comprising administering to a subject a effective mitosis or meiosis disrupting amount of a vanadium compound, preferably a vanadium cyclopentadienyl compound (vanadocene), or an oxovanadium compound. Exemplary compounds useful in the method of the invention are described, for example, in published PCT applications WO99/36063; WO 00/27389; and WO 00/35930. VDC and VDacac are specific compounds useful in the method invention, as well as other compounds of the invention described below.

The invention are useful applications where disruption of meiosis or mitosis is advantageous, for example, the treatment and prevention of cancer and non-cancer proliferative disorders including those described above, as well as in any other applications where the inhibition of mitosis and/or meiosis in cells is desired or useful.

DETAILED DESCRIPTION OF THE PREFERRED EMBODIMENT

The present invention is drawn to the use of vanadium compounds, preferably vanadium cyclopentadienyl compounds (vanadocenes) and oxovanadium compounds, including, but not limited to those described in published PCT applications WO99/36063; WO 00/27389; and WO 00/35930. Vanadium compounds useful in the method invention include vanadocene compounds such as vanadocene dichloride (VDC), vandocene acetylacetonate (VDacac), and those vanadium compounds shown below. Specifically, the present invention relates to the finding that these compounds effect disruption of normal mitotic and meiotic spindle formation, and are inhibitors of mitosis and meiosis. The anti-mitotic and anti-meiotic activity makes these compounds particularly attractive anti-proliferative agents, particularly for the treatment of non-cancer proliferative disorders.

Vanadium is a physiologically essential element that can be found in both anionic and cationic forms with oxidation states ranging from −3 to +5 (I—V). This versatility provides unique properties to vanadium complexes. In particular, the catonic form of vanadium complexes having an oxidation state of +4 (IV) has been shown to function as a modulator of cellular redox potential, to regulate enzymatic phosphorylation, and to exert pleiotropic effects in multiple biological systems by catalyzing the generation of reactive oxygen species (ROS). Besides the ability of vanadium metal to assume various oxidation states, its coordination chemistry also plays a key role in its interactions with various biomolecules. In particular, it is demonstrated herein that vanadium compounds, such as vanadium cyclopentadienyl compounds, or derivatives thereof, exhibit anti-mitotic and anti-meiotic properties. The effects of vandocene are primarily via disruption of mitotic and meiotic spindle formation.

Definitions

The following terms and phrases as used herein have the noted definitions, unless otherwise described:

"Halo" is fluoro, chloro, bromo, or iodo.

"Alkyl", "alkoxy", etc. denote both straight and branched hydrocarbon groups; but reference to an individual radical such as "propyl" embraces only the straight chain radical, a branched chain isomer such as "isopropyl" is specifically referenced.

"Organometallic compound" is an organic compound comprised of a metal attached directly to carbon (R—M).

"Coordination compound" is a compound formed by the union of a central metal atom or ion with ions or molecules called ligands or complexing agents.

"Ligand" or a "complexing agent" is a molecule, ion or atom that is attached to the central metal atom or ion of a coordination compound.

"Monodentate ligand" is a ligand having a single donor atom coordinated to the central metal atom or ion.

"Bidentate ligand" is a ligand having two donor atoms coordinated to the same central metal atom or ion.

"Vanadocene" is a compound having a central vanadium metal ion coordinated with at least two cyclopentadiene groups.

"Non-cancer proliferative disorder" includes such disorders as non-cancer proliferative disorders such as epithelial hyperplasia, polycytemia, erythrocytemia, thrombocytemia, EBV transformed lymphoproliferative syndrome, dysplastic nevus syndrome, restenosis after angioplasty for coronary heart disease, mastocytosis, histiocytosis, psoriasis, polyps, and the like.

It will be appreciated that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein. Methods to prepare optically active forms are known, for example, by resolution of the racemic form by recrystallization techniques, by synthesis from optically-active starting materials, by chiral synthesis, or by chromatographic separation using a chiral stationary phase. Methods for determining anti-mitotic and anti-meiotic activity of a compound are known, for example, using the standard tests described herein, or other known tests.

Specific values listed below for radicals, substituents, and ranges, are for illustration only; they do not exclude other defined values or other values within defined ranges for the radicals and substituents.

For example, $(C_1-C_6)$ alkyl can be methyl, ethyl, propyl, isopropyl, butyl, iso-butyl, sec-butyl, pentyl, 3-pentyl, or hexyl; $(C_1-C_3)$ alkyl can be methyl, ethyl or propyl; halo $(C_1-C_3)$ alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; $(C_1-C_3)$ alkoxy can be methoxy, ethoxy, or propoxy; and $(C_2-C_6)$ alkanoyloxy can be acetoxy, propanoyloxy, butanoyloxy, isobutanoyloxy, pentanoyloxy, or hexanoyloxy.

The following glossary of vanadium compounds is provided to clarify terms used throughout the specification and provides a listing of exemplary vanadium compounds useful in the method invention:

| | Group A: Vanadocene dihalides |
|---|---|
| VDC | Vanadocene dichloride ($Cp_2VCl_2$) |
| VMDC | Bis (methyl cyclopentadienyl) vanadium dichloride [$(MeCp)_2VCl_2$] |
| VDB | Vanadocene dibromide ($Cp_2VBr_2$) |
| VDI | Vanadocene diiodide ($Cp_2VI_2$) |
| | Group B: Vanadocene di-pseudohalides |
| VDA | Vanadocene diazide [$Cp_2V(N_3)_2$] |
| VDCN | Vanadocene dicyanide ($Cp_2V(CN)_2$) |
| VDOCN | Vanadocene dioxycyanate ($Cp_2V(OCN)_2$) |
| VDSCN | Vanadocene dithiocyanate ($Cp_2V(SCN)_2$) |
| VDSeCN | Vanadocene diselenocyanate ($VCp_2(SeCN)_2$) |
| | Group C: Vanadocene disubstituted derivatives |
| VDT | Vanadocene ditriflate ($Cp_2V(O_3SCF_3)_2$) |
| VDCO | Vanadocene monochloro oxycyanate ($Cp_2V(OCN)(Cl)$) |
| VDFe | Vanadocene monoacetonitrilo monochloro tetrachloro ferrate ($Cp_2VClNCCH_3)FeCl_4$ |
| | Group D: Chelated Vanadocene Complexes |
| VDacac | Vanadocene acetylacetonato monotriflate ($Cp_2V(CH_3COCH_2COCH_3)(O_3SCF_3)$ |
| VDBPY | Vanadocene bipyridino ditriflate ($CP_2V(C_{10}H_8N_2)(O_3SCF_3)_2$) |
| VDHfacac | Vanadocene hexafluoro acetylacetonato monotriflate $Cp_2V(CF_3COCH_2COCF_3)(O_3SCF_3)$) |
| VDH | Vanadocene acethydroxamato monotriflate ($Cp_2V(CH_3CON(O)H)(O_3SCF_3)$ |
| VDPH | Vanadocene N-phenyl benzohydroxamato monotriflate ($Cp_2V(C_6H_5CON(O)C_6H_5)(O_3SCF_3)$ |
| | Group E. Oxovanadium Compounds |

[VO(phen)] = (diaqua)(1,10-phenanthroline)oxovanadium (IV) sulfate;
[VO(phen)$_2$] = (aqua)bis(1,10-phenanthroline)oxovanadium (IV) sulfate;
[VO(Me$_2$-phen)] = (diaqua)(4,7-dimethyl-1,10-phenanthroline)-oxovanadium (IV) sulfate;
[VO(Me$_2$-phen)$_2$] = (aqua)bis(4,7-dimethyl-1,10-phenanthroline)-oxovanadium (IV) sulfate;
[VO(Cl-phen)] = (diaqua)(5-chloro-1,10-phenanthroline)-oxovanadium (IV) sulfate;
[VO(Cl-phen)$_2$] = (aqua)bis(5-chloro-1,10-phenanthroline)-oxovanadium (IV) sulfate;
[VO(bipy)] = (diaqua)(2,2'-bipyridyl)oxovanadium (IV) sulfate;
[VO(bipy)$_2$] = (aqua)bis(2,2'-bipyridyl)oxovanadium (IV) sulfate;
[VO(Me$_2$-bipy)] = (diaqua)(4,4'-dimethyl-2,2'-bipyridyl)-oxovanadium (IV) sulfate;
[VO(Me$_2$-bipy)$_2$] = (aqua)bis(4,4'-dimethyl-2,2'-bipyridyl)-oxovanadium (IV) sulfate;
[VO(Br,OH-acph)$_2$] = bis(5'-bromo-2'-hydroxyacetophenone)-oxovanadium (IV).

Unless otherwise indicated, the following abbreviations are used throughout the remainder of the disclosure:

Cp, cyclopentadienyl
Cp$^-$, cyclopentadienyl anion
acac, acetonylacetonate
Bpy, 2,2' Bipyridine
Hfacac, hexafluoroacetylacetonate
Cat, catecholate Dtc, diethyl dithio carbamate
Phen, phenanthroline
PH, N-phenyl benzohydroxamic acids
H, acetohydroxamic acid
OTf, trifluoromethane sulphonate
THF, tetrahydrofuran
DMSO, dimethyl sulfoxide
CH$_3$CN, acetonitrile
CH$_2$Cl$_2$, dichloromethane
d-d, laportte spin forbidden transitions
LMCT, ligand to metal charge transfer transitions
p-p*, intraligand charge transfer transitions The present invention concerns vanadium compounds, and the finding that such compounds have potent and selective anti-mitotic activity, and are particularly active and stable agents for use in the treatment or inhibition of proliferative type cellular disorders, for example, cancer, pathologic hyperplasia, etc.

The vanadium compounds of the invention are also useful for disrupting or inhibiting meiosis, where disruption of meiosis is desired or useful Vanadium (IV) compounds for use in this invention are as shown in formula I and formula II:

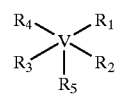

(I)

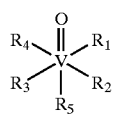

(II)

where R$_1$ and R$_2$ are each independently a monodentate ligand or together form a bidentate ligand; R$_3$ and R$_4$ are each independently a monodentate ligand or together form a bidentate ligand; and R$_5$ is a monodentate ligand, or is absent.

Suitable monodentate ligands include monodentate ligands are selected from the group consisting of halo, OH$_2$, O$_3$SCF$_3$, N$_3$, CN, OCN, SCN, SeCN, and a cyclopentadienyl ring, wherein each cyclopentadienyl ring is optionally substituted with one or more (C$_1$–C$_3$)alkyl. Suitable bidentate ligands are selected from the group consisting of acac, Bpy, Hfacac, Cat, Dtc, PH, H, and Phen, or derivatives thereof. The bidentate ligands may be substituted, for example, with one or more (C$_1$–C$_3$) alkyl, halo, (C$_1$–C$_3$) alkoxy, and halo (C$_1$–C$_3$) alkyl, and derivatives thereof. Halo is chloro, bromo, or iodo, and preferably is chloro.

In one embodiment, a useful vanadium compound has the following structure:

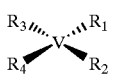

(III)

where R$_1$ and R$_2$ are each independently a monodentate ligand or together form a bidentate ligand; and R$_3$ and R$_4$ are each independently a cyclopentadienyl ring, wherein each cyclopentadienyl ring is optionally substituted with one or more (C$_1$–C$_3$)alkyl. In some preferred embodiments, R$_1$ and R$_2$ are each independently a monodentate ligand selected from the group consisting of of halo, OH$_2$, O$_3$SCF$_3$, N$_3$, CN, OCN, SCN, SeCN, and a cyclopentadienyl ring, where each cyclopentadienyl ring is optionally substituted with one or more (C$_1$–C$_3$)alkyl. Preferably, R$_1$ and R$_2$ arehalo, and more preferably are chloro.

In some other embodiments, R$_1$ and R$_2$ together form a bidentate ligand selected from the group consisting of acac, Bpy, Hfacac, Cat, Dtc, PH, H, and Phen, or derivatives thereof. Preferably, the bidentate ligand is acac, or derivatives thereof.

Some specific examples of compounds of formula I are: VCp$_2$Cl$_2$ (VDC), VCp$_2$Br$_2$, VCp$_2$I$_2$, VCp$_2$(N$_3$)$_2$, VCp$_2$(CN)$_2$, VCp$_2$(NCO)$_2$, VCp$_2$(NCO)Cl, VCp$_2$(NCS)$_2$, VCp$_2$(NCSe)$_2$, VCp$_2$Cl(CH$_3$CN)(FeCl$_4$), VCp$_2$(O$_3$SCF$_3$)$_2$, V(MeCP)$_2$Cl$_2$, V(Me$_5$Cp)$_2$Cl$_2$, VCp$_2$(acac) (VDacac), VCp$_2$(hf-acac), VCp$_2$(bpy), VCp$_2$(cat), VCp$_2$(dtc), VCp$_2$PH, or VCp$_2$H. Two particularly useful vandocene compounds are VDC and VDacac.

Useful oxovanadium compounds of formula II include the compound has the following structure:

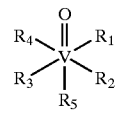

where R$_1$ and R$_2$ are each independently a monodentate ligand or together form a bidentate ligand; R$_3$ and R$_4$ together form a bidentate ligand; and R$_5$ is a monodentate ligand, or is absent. Preferably, R$_1$ and R$_2$ are each independently a monodentate ligand selected from the group consisting of halo, OH$_2$, O$_3$SCF$_3$, N$_3$, CN, OCN, SCN, SeCN, and a cyclopentadienyl ring, wherein each cyclopentadienyl ring is optionally substituted with one or more (C$_1$–C$_3$)alkyl, and R$_3$ and R$_4$ together form a bidentate ligand selected from the group consisting of acac, Bpy, Hfacac, Cat, Dtc, PH, H, and Phen, or derivatives thereof. Where R$_1$ and R$_2$ together form a bidentate ligand, the bidentate ligand is selected from the group consisting of acac, Bpy, Hfacac, Cat, Dtc, PH, H, and Phen, or a derrivative thereof.

Specific compounds of formula II include [VO(phen)], [VO(phen)$_2$], [VO(Me$_2$-phen)], [VO(Me$_2$-phen)$_2$], [VO(Cl-phen)], [VO(Cl-phen)$_2$], [VO(bipy)], [VO(bipy)$_2$], [VO(Me$_2$-bipy)], [VO(Me$_2$-bipy)$_2$], and [VO(Br,OH-acph)$_2$].

Compositions comprising these vanadium compounds are useful to inhibit mitosis and miosis, and thus are useful in the treatment of numerous proliferative cellular disorders in animals, and in particular mammals. Administration of the compounds as salts may be appropriate. Examples of acceptable salts include alkali metal (for example, sodium, potassium or lithium) or alkaline earth metal (for example calcium) salts, however, any salt that is non-toxic and effective when administered to the animal being treated is acceptable.

Acceptable salts may be obtained using standard procedures well known in the art, for example by reacting a sufficiently acidic compound with a suitable base affording a physiologically acceptable anion.

The compositions of the invention can be formulated as pharmaceutical compositions and administered to an animal host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained. When administered orally, the compositions of the invention can preferably be administered in a gelatin capsule.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compositions of the invention may also be administered intravenously or intraperitoneally by infusion or injection. Solutions of the active composition can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like.

In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active composition in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compositions may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compositions of the invention in a liquid composition, such as a lotion, will be from about 0.1–50 wt-%, preferably from about 0.5–5 wt %. The concentration in a semi-solid or solid composition such as a gel or a powder will be about 0.1–5 wt-%, preferably about 0.5–2.5 wt-%.

The amount of the composition required for use in treatment will vary not only with the particular salt selected but also with the route of administration, the nature of the condition being treated, and the age and condition of the patient, and will ultimately be at the discretion of the attendant physician or clinician.

In general, however, a suitable dose will be in the range of from about 0.1 to about 150 mg/kg, e.g., from about 10 to about 75 mg/kg of body weight per day, such as 3 to about 50 mg per kilogram body weight of the recipient per day, preferably in the range of 1 to 100 mg/kg/day, most preferably in the range of 5 to 20 mg/kg/day.

The compositions are conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Following i.m. administration, the compositions of the invention enter the blood stream within about 10–15 minutes and reach a maximum concentration in the blood within one hour of administration, at which point they can be found throughout the circulatory related organs.

EXAMPLES

The present invention may be better understood with reference to the accompanying examples that are intended for purposes of illustration only and should not be construed to limit the scope of the invention, as defined by the claims appended hereto.

Example 1

Synthesis of Vanadium Compounds

Compounds useful in the invention may be prepared by known methods, as described, for example, in published PCT Applications WO99/36063; WO 00/27389; and WO 00/35930. For example, VDC (VCp$_2$Cl$_2$) and [VCp$_2$(acac)] (CF$_3$SO$_3$); (VDacac) were prepared by following literature procedures (Wilkinson et al., *J. Am. Chem. Soc.*, 76: 4281–4284, 1954; Doyle et al., *Inorg. Chem.*, 7: 2479–2484, 1968) and purity was confirmed by $^1$H NMR, IR spectroscopy, and elemental analysis.

Example 2

Inhibition of Mitosis

This example illustrates inhibition of mitosis in eucaryotic cells administered vanadium compounds. In particular, VDC and VDacac inhibited cell division in Zebrafish embryos. This inhibition was concentration dependent.

The embryonic development of the Zebrafish (Danio rerio) is thoroughly studied and staged (Westerfield, M., *The Zebrafish Book*, 2nd edition. Eugene, Oreg.: Univ. of Oregon Press, 1993; Benyumov et al., Rus. *J. Dev. Biol.*, 26: 132–138, 1995; Winey et al., *J. Celll Biol.*, 114: 745–754, 1991). In Zebrafish meroblastic eggs, rapid cell divisions occur after the ooplasmic segregation on the animal pole of the egg cell, resulting within the first 3 hours of development in generation of a multicellular blastula comprised of several thousand cells.

The first series of cell divisions at the initial cleavage stage are approximately synchronous, only 15 minutes apart, and each set of the dividing blastomeres is characterized by a distinct pattern of cellular localization. This remarkable proliferation rate of undifferentiated eukaryotic vertebrate cells makes the Zebrafish embryo an attractive experimental model for evaluation of new agents for anti-proliferative activity. Therefore, in order to determine the utility of vanadium compounds as anti-mitotic agents, the effect of these compounds on the embryonic development of Zebrafish was examined.

Fish and Embryos

Adult, wild type Zebrafish were maintained generally according to the "Zebrafish Book" recommendations (Westerfield, M., *The Zebrafish Book*, Supra). Males and females were kept in 10 gallon tanks (70 fish per tank) with a constant slow flow of conditioned water at 26° C. and a controlled 14 h day/10 h night cycle. The fish were fed twice a day with live brine shrimp (Ocean Star International, Snowville, Utah). Breeding of one and the same group of fish occurred once in 2 weeks. With this breeding schedule, the Zebrafish embryos were obtained daily through (a) natural spawning at 28.5° C. in the breeding tanks with a netted false bottom or (b) fertilization in vitro using eggs and milt collected from the mature females and males anesthetized with Tricaine (Sigma, St. Louis, Mo.).

Zebrafish Embryo Model System

Two-cell stage Zebrafish embryos were dechorionated with 1% trypsin-EDTA and treated with 1% DMSO at a temperature of 28.5° C. Zebrafish embryos were removed from their chorions by mild digestion in 1% Trypsin-EDTA (Sigma, St. Louis, Mo.) for 10 minutes at 28.5° C. (Standard temperature - ST), washed three times in "egg water" and twice in "embryonic medium" (EM) as described in Westerfield, M., *The Zebrafish Book*, Supra. The dechorionated two-cell stage cleaving eggs/embryos were transferred to the 24-well plastic cell culture plates (Costar, Cambridge, Mass.) filled with EM. Dechorionated embryos (10–12 per well) were exposed to VDC and VDacac at a constant ST for 0.5–24 hours. The final volume of the medium in each well was 500 $\mu$L. Both compounds were used at concentrations ranging from 10 $\mu$M to 4 mM. The compounds were dissolved in DMSO and then diluted serially with the incubation medium. The final concentration of DMSO in the wells was 1.2%. The sham-treated control embryos were incubated in EM in the presence of 1.2% DMSO.

Microinjection of Zebrafish Embryos

VDC and VDacac were microinjected into Zebrafish embryos at room temperature, using a SMZ-10A stereo microscope (Nikon, Melville, N.Y.) and Transjector 5246 (Eppendorf, Westbury, N.Y.). Dechorionated Zebrafish embryos at the two-cell stage were transferred to a Petri dish filled with embryonic medium. The bottom of the Petri dish was covered with an agar layer, and the embryos were placed in grooves in agar, exactly as described in Westerfield, M., *The Zebrafish Book*, Supra. Microinjections were performed under visual control. At the 2–4 cell stage, approximately 2 nL of the compound dissolved in Hank's Balanced Salt Solution (HBSS) (Gibco, Rockville, Md.) with 10% DMSO was injected into the cytoplasm of one of the blastomeres through a constantly flowing micropipette with a splinted sharp tip of 2–3 $\mu$m diameter. Sham-treated control embryos were injected with 2 nL of HBSS containing 10% DMSO. After the treatment, the embryos were transferred to standard temperature, 28.5° C.

Observation of Zebrafish Embryo Cell Division

Observations of cell division and development of the Zebrafish embryos were carried out using a SMZ-10A stereo microscope, once every 30 minutes within the first 3 hours of incubation and at 6, 12 and 24 hours, as well. The drug effect was considered to be revealed when all embryos from one well were affected in a characteristic manner in 3 independent experiments. The stereo microscope was fitted with a specially designed transparent heating tray in order to keep embryos at ST during observations. Pictures of the embryos were taken with a H-III Photomicrographic System (Nikon) using Ektachrome 64X film (Kodak, Rochester, N.Y.).

Results

Normal cell division and development proceeded in control Zebrafish embryos exposed to vehicle alone. At 60 minutes post fertilization the embryos had reached the 4-cell stage. Fifteen minutes later, the embryos have reached the eight cell stage. Two hours after fertilization the embryos had reached the 64 cell stage, and 200 minutes after fertilization the embryos had reached the blastula stage. Just seven hours after fertilization the embryo was midway through the gastrula stage and hasdcompleted 70% epiboly.

In treated embryos, the vanadium compound VDC as well as VDacac inhibited mitosis in a concentration-dependent fashion. Thirty minutes after treatment, control embryos had developed to the 8-cell stage. Embryos treated with 1.9 mM VDC or 0.6 mM VDacac showed cell division defects followed by fusion of the embryonic cells. At lower concentrations cellular effects were less rapid and severe but still evident. After 120 minutes of incubation control embryos reached the high blastula stage forming a compact multicellular blastoderm on the animal pole of the egg. Embryos treated with 0.76 mM VDC for 120 minutes developed abnormal blastulae. In these embryos, cell division was found only on top of the blastodisc and fusion of cells occurred in the periphery of the blastodisc and in the deep layers adjacent to the yolk cell. Embryos treated with 0.4 mM VDacac for 120 minutes developed similar defects. In these embryos, impaired blastoderm formation and loss of cell compaction were observed.

The anti-proliferative effects of vanadium compounds microinjected into the cytoplasm of two-cell stage Zebrafish embryos was next examined. Microinjection of VDC into the Zebrafish embryo caused concentration dependent defects in embryonic development. Zebrafish embryos were microinjected with 0.64 pmol, 32 pmol, and 58 pmol of VDC. The lowest concentration caused formation of a blastocoel-like cavity in the blastoderm and prevented gastrulation. A higher concentration led to cell division slowdown and total disarray of cell localization and development arrest and the highest concentration caused total cell fusion within 30 minutes of microinjection. Similar results were observed after microinjection of 1 pmoL and 49 pmoL VDacac. Lower concentrations caused formation of a blastocoel-like cavity in the blastoderm and prevented gastrulation. Higher concentrations led to deterioration of cell localization and development failure.

The data demonstrates that the vanadium compounds of the present invention are potent inhibitors of mitosis (cell division) in cells that have high rates of cell division, and that this inhibition occurs in a specific and concentration dependent manner.

Example 3

Disruption of Meiotic Spindle Formation by Vanadium Compounds

This example illustrates disruption of meiotic spindle formation in cells administered vanadium comounds of the invention. In particular, VDC disrupted meiotic spindle formation and cell division in germinal vesicle stage bovine oocytes.

In vitro Maturation and Treatment of Bovine Oocytes

Immature oocytes were recovered from bovine ovaries after slaughter by aspiration of 5 mm follicles. Only oocytes having a homogenous cytoplasm and surrounded by at least three layers of cumulus cells were selected. These were washed through three rinses of Hepes buffered Tyrode's media (114 mM NaCl, 3.2 mM KCl, 2 mM $CaCl_2 2H_2O$, 5 mM $MgCl_2 6H_2O$, 25 mM $NaHCO_3$, 0.4 mM $NaH_2PO_4$, 10 mM Na lactate, 100 I.U./ml Penicillin)(TL-Stock) modified with 10 mM Hepes, 1 mg/ml BSA, 0.2 mM pyruvate, and 25 $\mu$g/ml gentamicin (TL-Hepes; (16). Oocytes were matured for 24 hours in 50 $\mu$l drops of TC199 modified with 10% fetal bovine serum, 5 $\mu$g/ml FSH-p, 25$\mu$g/ml gentamicin, 1 $\mu$g/ml estrogen at 39° C. in 5% $CO_2$ under mineral oil (17). After the oocytes were placed in the drops, 25 or 50 $\mu$M VDC was added in DMSO. Equal amounts of DMSO were added to control drops. Bovine oocytes were processed for immunocytochemistry after 24 hours.

Germinal vesicle stage bovine oocytes were matured in vitro in the presence of vehicle or VDC (25 $\mu$M or 50 $\mu$M). After 24 hours, these oocytes were fixed, labeled with anti-tubulin antibodies and the DNA dye TOTO-3. Oocytes were scored according to their stage in meoisis, microtubule organization and chromosome number.

Results

Control oocytes completed maturation and arrested at metaphase of meiosis II (MII) 93% of the time. In contrast, only 16.2% and 10.0% of oocytes exposed to 25 $\mu$M and 50 $\mu$M VDC, respectively, matured to MII and the remainder were arrested at the metaphase of meiosis I (MI).

When oocytes were evaluated for proper meiotic spindle formation, only 4% of vehicle-treated control oocytes had malformed MI or MII meiotic spindles. By comparison, 50% or more of oocytes treated with VDC (25 or 50 $\mu$M) had abnormal meiotic spindles. Representative examples of the meiotic spindles were further studied. Some of the aberrant MI spindles were very well organized. Representative aberrant oocytes had 6 separate spindles nucleated from 4 organizing centers. Other MI spindles were only loosely organized. Some spindles were normal except for being a MI spindle after 24 hours of maturation consistent with an inappropriate maturational arrest. An example of a properly arrested MII spindle was examined for comparison purposes, and it was noted that the normal spindle was small, bipolar and oriented tangentially to the plasma membrane.

The data indicates that the vanadium compound VDC has a disruptive influence on meiotic spindle formation, and further indicates that treatment with vanadium compounds such as VDC is effective to block continued eucaryotic oocyte development.

Example 4

Inhibition of Mitotic Spindle Formation

This example illustrates disruption of mitotic spindle formation on administration of vanadium compounds. In particular, administration of VDC or VDacac inhibited proliferation of human breast cancer and glioblastoma cells. The inhibition occurred through disruption of the mitotic spindle.

Cell Culture and Treatment

BT-20 and MDA-MB-231 breast cancer cells (HTB-19, HTB-26 ATCC, Rockville, Md.) and U373 glioblastoma cells (HTB-17 ATCC Rockville, Md.) were grown in MEM media modified with 10% Fetal Bovine serum and 1% Penicillin/Streptomycin (Life Technologies, Rockville Md.). Cells were seeded onto sterile 22 mm square coverslips in 6-well plates. Cells on coverslips were kept in an incubator for 24 hours prior to treatment. The following day, VDC or VDacac was added from a stock solution made in DMSO to yield final concentration ranging from 3.9 to 500 µM (final DMSO concentration=0.025%). Cells were returned to a 37° C. incubator for 24 hours.

Cytotoxicity Assay

The cytotoxicity of VDC and VDacac against the human tumor cell lines discussed above was assayed using the MTT (3-[4,5-dimethylthiazol-2-yl]-2,5-diphenyl tetrazolium bromide) assay (Boehringer Mannheim Corp., Indianapolis, Ind.). Briefly, exponentially growing tumor cells were seeded into a 96-well plate at a density of $2.5 \times 10^4$ cells/well and incubated for 36 hr at 37° C. prior to drug exposure. On the day of treatment, culture medium was carefully aspirated from the wells and replaced with fresh medium containing VDC or VDacac at concentrations ranging from 3.9 to 500 µM. Triplicate wells were used for each treatment. The cells were incubated with the vanadium compounds for 48 hours at 37° C. in a humidified 5% $CO_2$ atmosphere. To each well, 10 µl of MTT (0.5 mg/ml final concentration) was added and the plates were incubated at 37° C. for 4 hours to allow MTT to form formazan crystals by reacting with metabolically active cells. The formazan crystals were solubilized overnight at 37° C. in a solution containing 10% SDS in 0.01 M HCl. The absorbence of each well was measured in a microplate reader (Labsystems, Helsinki, Finland) at 540 nm and a reference wavelength of 690 nm. To translate the $OD_{540}$ values into the number of live cells in each well, the $OD_{540}$ values were compared to those on standard $OD_{540}$—versus—cell number curves generated for each cell line. The percent survival was calculated using the formula: % survival=Live cell number[test]/Live cell number [control]× 100. The $IC_{50}$ values were calculated by non-linear regression analysis using Graphpad Prism software version 2.0 (Graphpad Software, Inc., San Diego, Calif.).

Immunocytochemistry and Confocal Microscopic Analysis

At the appropriate time point, coverslips containing BT-20 cells were fixed in -20° C. methanol for 15 minutes followed by 15 minutes incubation in phosphate buffered saline +0.1% Triton X-100 (PBS+Tx). Coverslips were next incubated with a primary antibody recognizing α-tubulin (Sigma, St.Louis Mo.) γ-tubulin (BAbCo, Berkeley Calif.), or NuMA (Calbiochem, SanDiego Calif.) for 40 minutes in a humidified chamber at 37° C. Coverslips were washed for 15 minutes in PBS-Tx followed by a 40 min incubation with a fluorescently labeled secondary antibody (Jackson Immunoresearch, West Grove Pa.). For double labeling the respective primary and secondary antibodies were combined. The coverslips were again rinsed in PBS-Tx and incubated with 5 µM Toto-3 (Molecular Probes, Eugene Oreg.) for 20 minutes to label the DNA. Coverslips were immediately inverted onto slides in Vectashield (Vector Labs, Burlingame, N.H.) to prevent photobleaching, sealed with nail polish and stored at 4° C. Bovine oocytes were processed for immunocytochemistry as described previously. Navara et al., Dev. Biol., 162: 29–40, 1994.

Slides were examined using a Bio-Rad MRC-1024 Laser Scanning Confocal Microscope mounted on a Nikon Eclipse E800 upright microscope with high numerical aperture objectives. Digital data was processed using Lasersharp (Bio-Rad, Hercules Calif.) and Photoshop (Adobe Systems Mountain View Calif.) software and printed on a Pictrography printer (Fuji Photo Elmsford, N.Y.).

Results

As shown below, VDC and VDacac inhibited cellular proliferation of the breast cancer cells MDA-MB-231 and BT-20 as well as the glioblastoma cells U373 in a concentration-dependent fashion.

|  | MDA-MB-231 ($IC_{50}$) | BT20 ($IC_{50}$) | U373 ($IC_{50}$) |
| --- | --- | --- | --- |
| VDC | 11.0 µM | 14.9 µM | 18.6 µM |
| VDacac | 9.1 µM | 26.9 µM | 35.5 µM |

The mitotic spindles of vehicle-treated and vanadocene-treated BT-20 breast cancer cells was examined using confocal laser scanning microscopy. Vehicle-treated control cells showed mitotic spindles that were organized as a bipolar microtubule array, and the DNA was organized on a metaphase plate. VDC-treated and VDacac treated BT-20 cells showed aberrant monopolar mitotic structures, where microtubules were detected only on one side of the chromosomes and the chromosomes were arranged in a circular pattern.

In yeast, monopolar spindles have been shown to arise either from a failure of the centrosome to duplicate or a failure of the duplicated centrosomes to separate correctly. Winey et al., J. Cell Biol., 114: 745–754, 1991; Glover et al, Cell, 81: 95–105, 1995. In order to distinguish between these two possibilities, BT-20 cells were labeled for the spindle pole marker γ-tubulin. Control cells showed a single focus of γ-tubulin at each pole of the bipolar mitotic spindle. In contrast, VDC-treated cells had two foci of γ-tubulin on the same side of the chromosomes resulting in a broad centrosome at one pole. All monopolar spindles examined had two foci of γ-tubulin labeling consistent with a mechanism in which the centrosomes duplicate but do not separate properly to form a bipolar spindle.

To further confirm the absence of a centrosome on the other side of the aspindle the localization of the mitotic apparatus protein NuMA was examined. NuMa in control cells localizes in a crescent shaped pattern at both poles of the condensed chromosomes at the mitotic spindle poles. In contrast, NuMa in cells treated with VDC was only localized to one side of the mitotic spindle, confirming the lack of a functional centrosome on the other side of the spindle.

The data demonstrates the potent anti-mitotic properties of vanadium compounds and that the mechanism of action involves disruption of mitotic spindle formation. Accordingly, these vanadium compounds are effective anti-mitotic agents.

Example 5

ATPase Activity of the Mocrotubule Motor Protein Dynein is not Inhibited

This example illustrates that the disruptive influence of the vanadium compounds on the mitotic spindle does not occur via inhibition of ATPase activity in the dynein motor protein.

Proper bipolar spindle formation is dependent on the microtubule motor protein dynein. Monopolar spindles have been observed in cells microinjected with specific antibodies that inhibit the function of this motor protein (Vaisberg et al., J. Cell Biol., 123: 849–858, 1993). Therefore, to determine if dynein was involved in the VDC mediated formation of monopolar spindles the effect of VDC on the ATPase activity of dynein was examined. Dynein is found in large quantities in the axonemes of sperm and is the predominant ATPase found in sperm axonemes.

Phosphate Assay

The effect of VDC on ATPase and GTPase activity was determined by isolating sperm axonemes after treatment of human sperm with 100 μM VDC. Sperm were pelleted by centrifugation 1900×g for 15 min, washed twice in cold PBS, resuspended in extraction buffer (1.0% Triton X-100, 0.1 M NaCl, 4 mM MgSO4, 1 mM CaCL2, 0.1 mM EDTA, 0.1 mM ATP, 7 mM 2-mercaptoethanol, and 5 mM imidazole buffer pH 7.0) and disrupted using a Dounce homogenizer. This homogenized suspension was centrifuged at 1500×g for 5 min to remove sperm heads and the resulting supernatant was recentrifuged at 12,000×g to recover the broken axonemes.

The axoneme pellet was resuspended in extraction buffer to remove residual membrane material, centrifuged at 1500×g for 5 min to remove residual sperm heads followed by centrifugation at 12,000×g to recover axonemes. The recovered axonemes were washed three times in extraction buffer lacking Triton X-100 and resuspended in solubilization buffer (0.6 M NaCl, 4 mM MgSO4, 1 mM CaCl2, 0.1 mM EDTA, 1 mM DTT, 7 mM 2-mercaptoetanol, 5 mM imidazole buffer pH 7.0) to solubilize the readily extractable motor protein dynein. The suspension was then centrifuged at 12,000×g. The resulting supernatant was clarified by centrifugation at 100,000×g for 15 minutes. ATPase activity was measured using the EnzChek Phophate assay kit (Molecular Probes, Eugene Oreg.) according to manufacturers instructions.

Results

In four separate experiments, 100 μM VDC inhibited the ATPase activity found in axonemes by only 12.2% (0.08±0.01 vs 0.07±0.02). Therefore, it is unlikely that inhibition of dynein is the mode of action of monopolar spindle formation in tumor cells treated with these vanadium compounds.

The formation of monopolar mitotic spindles can be broken down into two categories; those without replicated centrosomes and those with replicated centrosomes. The first category is exemplified by those caused by mutations of mps1/mps2 (Winey et al, *J. Cell Biol.*, 114: 745–754, 1991) and cdc31 in yeast (Byers et al., Alfred Benzon Symposium, 16: 119–133, Copenhagen:Munksgaard, 1981). In these cases, the spindle pole body, the yeast equivalent of the animal cell centrosome, fails to duplicate properly and a monopolar spindle is formed. The second category includes the aur (Glover et al., *Cell*, 81: 95–105, 1995) and dal (Sullivan et al., Development, 110: 311–323, 1990) mutations in drosophila. In these cases, the centrosome duplicates but does not separate properly forming a monopolar spindle. VDC-generated monopolar spindles fall into the second category. Labeling cells with the invariant centrosomal marker γ-tubulin clearly shows two centrosomes at the single pole.

VDC also affects meiotic spindle formation. Meiotic spindles are formed in a different fashion and under different regulation than are mitotic spindles. The largest difference is that virtually all microtubule nucleation in mitotic cells originates from the centrosome. Therefore, if the centrosome is not replicated or separated correctly, spindle formation is affected. In contrast, the microtubule nucleating materials in mammalian oocytes are scattered throughout the cytoplasm. Schatten, G., Dev. Biol., 165: 299–335, 1994. Isolated chromosomal pairs have been shown to organize bipolar spindles when injected into meiotic cells. Church et al., *J. Cell Biol.*, 103: 2765–2773, 1986. Despite these differences in spindle formation, meiotic spindle formation is also affected. Hence, VDC likely inhibits a component common to both types of spindle formation.

These results indicate a novel mechanism for inhibition of spindle formation by organometallic compounds and establish vanadium compounds such as vanadium compounds as a new class of antiproliferative agents which block centrosome separation in mitotic cells and also block proper spindle formation in meiotic cells. These compounds warrant further investigation as antiproliferative agents.

The above specification, examples and data provide a complete description of the manufacture and use of the composition of the invention. Since many embodiments of the invention can be made without departing from the spirit and scope of the invention, the invention resides in the claims hereinafter appended.

The specification recites numerous patents and publications, each which is expressly incorporated by reference as if fully set forth.

We claim:

1. A method for inhibiting mitosis or meiosis in a non-cancer cell comprising administering to the non-cancer cell an effective mitosis or meiosis inhibiting amount of a vanadium compound having the following structure:

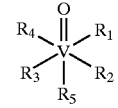

(II)

wherein, $R_1$ and $R_2$ are each independently a monodentate ligand or together form a bidentate ligand;

$R_3$ and $R_4$ are each independently a monodentate ligand or together form a bidentate ligand; and $R_5$ is a monodentate ligand, or is absent;

wherein at least one of $R_1$ and $R_2$ or $R_3$ and $R_4$ combine together to form a bidenate ligand selected from the group consisting of acac, Bpy, Hfacac, Cat, Dtc, PH, acetohydroxamic acid, Phen, or a derivative thereof.

2. The method of claim 1, wherein each monodentate ligand is selected from the group consisting of halo, $OH_2$, $O_3SCF_3$, $N_3$, CN, OCN, SCN, SeCN, and a cyclopentadienyl ring, wherein the cyclopentadienyl ring is optionally substituted with one or more $(C_1-C_3)$alkyl, and each bidentate ligand is selected from the group consisting of acac, Bpy, Hfacac, Cat, Dtc, PH, acetohydroxamic acid, Phen, or a derivative thereof.

3. The method of claim 2, wherein each bidentate ligand is optionally substituted with one or more of halo, $(C_1-C_3)$ alkyl, $(C_1-C_3)$ alkoxy, halo $(C_1-C_3)$ alkyl, or a derivative thereof.

4. The method of claim 1, wherein $R_1$ and $R_2$ together form a bidentate ligand selected from the group consisting of acac, Bpy, Hfacac, Cat, Dtc, PH, acetohydroxamic acid and derivatives thereof.

5. The method of claim 4, wherein the bidentate ligand is acac or a derivative thereof.

6. The method of claim 1, wherein said vanadium compound is: $VCp_2$(acac), $VCp_2$(hfacac), $VCp_2$(bpy), $VCp_2$(cat), $VCp_2$(dtc), $VCp_2$PH, or $VCp_2$H wherein H represents acetohydroxamic acid bidentate ligand.

7. A method for treating a non-cancer proliferative disorder in a subject, comprising administering to the subject an effective mitosis inhibiting amount of a vanadium compound of structure II:

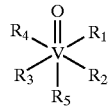

(II)

wherein,
- $R_1$ and $R_2$ are each independently a monodendate ligand or together form a bidendate ligand;
- $R_3$ and $R_4$ are each independently a monodendate ligand or together form a bidendate ligand; and
- $R_5$ is a monodendate ligand, or is absent;

wherein (i) at least one of $R_1$ and $R_2$ or $R_3$ and $R_4$ combine together to form a bidendate ligand selected from the group consisting of acac, Bpy, Hfacac, Cat, Dtc, PH, acetohydroxamic acid, Phen, or a derivative thereof, and (ii) at least one of $R_1$, $R_2$, $R_3$, $R_4$ or $R_5$ is a cyclopentadienyl ring.

* * * * *

UNITED STATES PATENT AND TRADEMARK OFFICE
CERTIFICATE OF CORRECTION

PATENT NO. : 6,642,221 B1
DATED : November 4, 2003
INVENTOR(S) : Uckun et al.

It is certified that error appears in the above-identified patent and that said Letters Patent is hereby corrected as shown below:

<u>Title page,</u>
Item [75], Inventors, "Faith M. Uckun," should read -- Fatih M. Uckun, --
Item [56], References Cited, FOREIGN PATENT DOCUMENTS, "WO 00/25930" should read -- WO 00/35930 --

Signed and Sealed this

Ninth Day of March, 2004

JON W. DUDAS
*Acting Director of the United States Patent and Trademark Office*